US011706265B2

United States Patent
Cheevers

(10) Patent No.: US 11,706,265 B2
(45) Date of Patent: Jul. 18, 2023

(54) COMPANION CAMERA AND MICROPHONE

(71) Applicant: ARRIS Enterprises LLC, Suwanee, GA (US)

(72) Inventor: Charles Peter Cheevers, Alpharetta, GA (US)

(73) Assignee: ARRIS ENTERPRISES llc, Suwanee, GA (US)

( * ) Notice: Subject to any disclaimer, the term of this patent is extended or adjusted under 35 U.S.C. 154(b) by 0 days.

(21) Appl. No.: 17/570,648

(22) Filed: Jan. 7, 2022

(65) Prior Publication Data

US 2022/0224736 A1 Jul. 14, 2022

Related U.S. Application Data

(60) Provisional application No. 63/137,315, filed on Jan. 14, 2021.

(51) Int. Cl.
| | |
|---|---|
| *H04L 65/403* | (2022.01) |
| *H04N 23/74* | (2023.01) |
| *H04N 23/56* | (2023.01) |
| *H04N 7/04* | (2006.01) |

(52) U.S. Cl.
CPC ............ *H04L 65/403* (2013.01); *H04N 7/04* (2013.01); *H04N 23/56* (2023.01); *H04N 23/74* (2023.01)

(58) Field of Classification Search
CPC .. H04L 65/403; H04N 5/2256; H04N 5/2354; H04N 7/147; H04N 7/141; H04N 7/04; H04N 23/56; H04N 23/74; A61B 5/0002; A61B 5/01; A61B 5/021
See application file for complete search history.

(56) References Cited

U.S. PATENT DOCUMENTS

| | | |
|---|---|---|
| 2012/0029303 A1 | 2/2012 | Shaya |
| 2015/0119652 A1 | 4/2015 | Hyde et al. |
| 2018/0353073 A1* | 12/2018 | Boucher .................. A61B 5/05 |
| 2019/0206558 A1 | 7/2019 | Hyde et al. |

OTHER PUBLICATIONS

International Search Report and the Written Opinion of the International Searching Authority dated Apr. 4, 2022 in International (PCT) Application No. PCT/US2022/011545.

* cited by examiner

*Primary Examiner* — Nelson D. Hernández Hernández
(74) *Attorney, Agent, or Firm* — Wenderoth, Lind & Ponack, L.L.P.

(57) ABSTRACT

A system and method are provided for a wireless device for use with a first video conference device, a second video conference device, WAN and an item. The video conference devices are configured to establish a video conference over a secure communication channel over the WAN. The first video conference device is additionally configured to transmit a video conference invitation in response to a video conference request from the wireless device, the video conference invitation including credentials to establish a communication channel with the first video conference device. The second video conference device is additionally configured to transmit a magnification control signal. The wireless device is configured to: image the item in a first magnification; transmit first image data of the item based on the first magnification; change the magnification; image the item in a second magnification; and transmit second image data of the item based on the second magnification.

12 Claims, 6 Drawing Sheets

COMPANION CAMERA AND MICROPHONE

BACKGROUND

Embodiments of the present disclosure relate to remotely controlling an authorized device's camera and light in a video conference.

SUMMARY

Aspects of the present disclosure are drawn to a wireless device for use with a first video conference device, a second video conference device, a wide area network ("WAN") and an item. The first video conference device and the second video conference device are configured to establish a video conference over a secure communication channel over the WAN. The first video conference device is configured to provide first video data and first audio data to the second video conference device during the video conference. The second video conference device is configured to provide second video data and second audio data to the first video conference device during the video conference. The first video conference device is additionally configured to display the second video data and to output the second audio data, and the second video conference device is additionally configured to display the first video data and to output the first audio data. The first video conference device is additionally configured to transmit a video conference invitation in response to a video conference request, the video conference invitation including credentials to establish a communication channel with the first video conference device. The second video conference device is additionally configured to transmit a magnification control signal. The wireless device includes a camera, a memory, and a processor. The camera is configured to: image the item in a first magnification; output first image data of the item based on the first magnification; change the magnification; image the item in a second magnification; and output second image data of the item based on the second magnification. The processor configured to execute instructions stored on the memory to cause the wireless device to: transmit the video conference request to the first video conference device; receive the video conference invitation; establish the communication channel with the first video conference device; transmit the first image data to the second video conference device; receive the magnification control signal; instruct the camera to change the magnification based on the magnification control signal; and transmit the second image data to the second video conference device.

In some embodiments, the second video conference device is additionally configured to transmit a lighting control signal. The wireless device further includes a light configured to provide a first illumination and to provide a second illumination. The processor is configured to execute instructions stored on the memory to additionally cause the wireless device to: instruct the light to provide the first illumination; receive the lighting control signal; instruct the light to provide the second illumination based on the lighting control signal.

Other aspects of the present disclosure are drawn to a method of using a wireless device with a first video conference device, a second video conference device, a WAN and an item. The first video conference device and the second video conference device are configured to establish a video conference over a secure communication channel over the WAN. The first video conference device is configured to provide first video data and first audio data to the second video conference device during the video conference. The second video conference device is configured to provide second video data and second audio data to the first video conference device during the video conference. The first video conference device is additionally configured to display the second video data and to output the second audio data, and the second video conference device is additionally configured to display the first video data and to output the first audio data. The first video conference device is additionally configured to transmit a video conference invitation in response to a video conference request, the video conference invitation including credentials to establish a communication channel with the first video conference device. The second video conference device is additionally configured to transmit a magnification control signal. The wireless device includes a camera, a memory, and a processor. The camera is configured to: image the item in a first magnification; output first image data of the item based on the first magnification; change the magnification; image the item in a second magnification; and output second image data of the item based on the second magnification. The processor configured to execute instructions stored on the memory to cause the wireless device to: transmit the video conference request to the first video conference device; receive the video conference invitation; establish the communication channel with the first video conference device; transmit the first image data to the second video conference device; receive the magnification control signal; instruct the camera to change the magnification based on the magnification control signal; and transmit the second image data to the second video conference device.

In some embodiments, the method, wherein the second video conference device is additionally configured to transmit a lighting control signal, further includes: providing, via a light, a first illumination; receiving, via the processor, the lighting control signal; and instructing, via the processor, the light to provide a second illumination based on the lighting control signal.

Other aspects of the present disclosure are drawn to a non-transitory, computer-readable media having computer-readable instructions stored thereon, the computer-readable instructions being capable of being read by a wireless device for use with a first video conference device, a second video conference device, a WAN and an item. The first video conference device and the second video conference device are configured to establish a video conference over a secure communication channel over the WAN. The first video conference device is configured to provide first video data and first audio data to the second video conference device during the video conference. The second video conference device is configured to provide second video data and second audio data to the first video conference device during the video conference. The first video conference device is additionally configured to display the second video data and to output the second audio data, and the second video conference device is additionally configured to display the first video data and to output the first audio data. The first video conference device is additionally configured to transmit a video conference invitation in response to a video conference request, the video conference invitation including credentials to establish a communication channel with the first video conference device. The second video conference device is additionally configured to transmit a magnification control signal. The wireless device includes a camera, a memory, and a processor. The camera is configured to: image the item in a first magnification; output first image data of the item based on the first magnification; change the magnification; image the item in a second magnification; and output second image data of the item based on the second magnification. The processor configured to execute instructions stored on the memory to cause the wireless device to: transmit the video conference request to the first video conference device; receive the video conference invitation; establish the communication channel with the first video conference device; transmit the first image data to the second video conference device; receive the magnification control signal; instruct the camera to change the magnification based on the magnification control signal; and transmit the second image data to the second video conference device.

In some embodiments, wherein the second video conference device is additionally configured to transmit a lighting control signal, the computer-readable instructions are capable of instructing the wireless device to perform the method further including: providing, via a light, a first illumination; receiving, via the processor, the lighting control signal; and instructing, via the processor, the light to provide a second illumination based on the lighting control signal.

Other aspects of the present disclosure are drawn to a wireless device for use with a first video conference device, a second video conference device, a WAN and an item. The first video conference device and the second video conference device are configured to establish a video conference over a secure communication channel over the WAN. The first video conference device is configured to provide first video data and first audio data to the second video conference device during the video conference. The second video conference device is configured to provide second video data and second audio data to the first video conference device during the video conference. The first video conference device is additionally configured to display the second video data and to output the second audio data, and the second video conference device is additionally configured to display the first video data and to output the first audio data. The first video conference device is additionally configured to transmit credentials to establish a communication channel with the wireless device. The second video conference device is additionally configured to transmit a magnification control signal. The wireless device includes a camera, a memory, and a processor. The camera is configured to: image the item in a first magnification; output first image data of the item based on the first magnification; change the magnification; image the item in a second magnification; and output second image data of the item based on the second magnification. The processor configured to execute instructions stored on the memory to cause the wireless device to: receive the credentials; establish the communication channel with the first video conference device; transmit the first image data to the second video conference device; receive the magnification control signal; instruct the camera to change the magnification based on the magnification control signal; and transmit the second image data to the second video conference device.

In some embodiments, the second video conference device is additionally configured to transmit a lighting control signal. The wireless device further includes a light configured to provide a first illumination and to provide a second illumination. The processor is configured to execute instructions stored on the memory to additionally cause the wireless device to: instruct the light to provide the first illumination; receive the lighting control signal; instruct the light to provide the second illumination based on the lighting control signal.

Other aspects of the present disclosure are drawn to a method of using a wireless device with a first video conference device, a second video conference device, a WAN and an item. The first video conference device and the second video conference device are configured to establish a video conference over a secure communication channel over the WAN. The first video conference device is configured to provide first video data and first audio data to the second video conference device during the video conference. The second video conference device is configured to provide second video data and second audio data to the first video conference device during the video conference. The first video conference device is additionally configured to display the second video data and to output the second audio data, and the second video conference device is additionally configured to display the first video data and to output the first audio data. The first video conference device is additionally configured to transmit credentials to establish a communication channel with the wireless device. The second video conference device is additionally configured to transmit a magnification control signal. The wireless device includes a camera, a memory, and a processor. The camera is configured to: image the item in a first magnification; output first image data of the item based on the first magnification; change the magnification; image the item in a second magnification; and output second image data of the item based on the second magnification. The processor configured to execute instructions stored on the memory to cause the wireless device to: receive the credentials; establish the communication channel with the first video conference device; transmit the first image data to the second video conference device; receive the magnification control signal; instruct the camera to change the magnification based on the magnification control signal; and transmit the second image data to the second video conference device.

In some embodiments, the method, wherein the second video conference device is additionally configured to transmit a lighting control signal, further includes: providing, via a light, a first illumination; receiving, via the processor, the lighting control signal; and instructing, via the processor, the light to provide a second illumination based on the lighting control signal.

Other aspects of the present disclosure are drawn to a non-transitory, computer-readable media having computer-readable instructions stored thereon, the computer-readable instructions being capable of being read by a wireless device for use with a first video conference device, a second video conference device, a WAN and an item. The first video conference device and the second video conference device are configured to establish a video conference over a secure communication channel over the WAN. The first video conference device is configured to provide first video data and first audio data to the second video conference device during the video conference. The second video conference device is configured to provide second video data and second audio data to the first video conference device during the video conference. The first video conference device is additionally configured to display the second video data and to output the second audio data, and the second video conference device is additionally configured to display the first video data and to output the first audio data. The first video conference device is additionally configured to transmit credentials to establish a communication channel with the wireless device. The second video conference device is additionally configured to transmit a magnification control signal. The wireless device includes a camera, a memory, and a processor. The camera is configured to: image the item in a first magnification; output first image data of the item based on the first magnification; change the magnification; image the item in a second magnification; and output second image data of the item based on the second magnification. The processor configured to execute instructions stored on the memory to cause the wireless device to: receive the credentials; establish the communication channel with the first video conference device; transmit the first image data to the second video conference device; receive the magnification control signal; instruct the camera to change the magnification based on the magnification control signal; and transmit the second image data to the second video conference device.

In some embodiments, wherein the second video conference device is additionally configured to transmit a lighting control signal, the computer-readable instructions are capable of instructing the wireless device to perform the method further including: providing, via a light, a first illumination; receiving, via the processor, the lighting control signal; and instructing, via the processor, the light to provide a second illumination based on the lighting control signal.

BRIEF SUMMARY OF THE DRAWINGS

The accompanying drawings, which are incorporated in and form a part of the specification, illustrate example embodiments and, together with the description, serve to explain the principles of the present disclosure. In the drawings.

DETAILED DESCRIPTION

Figure 1:
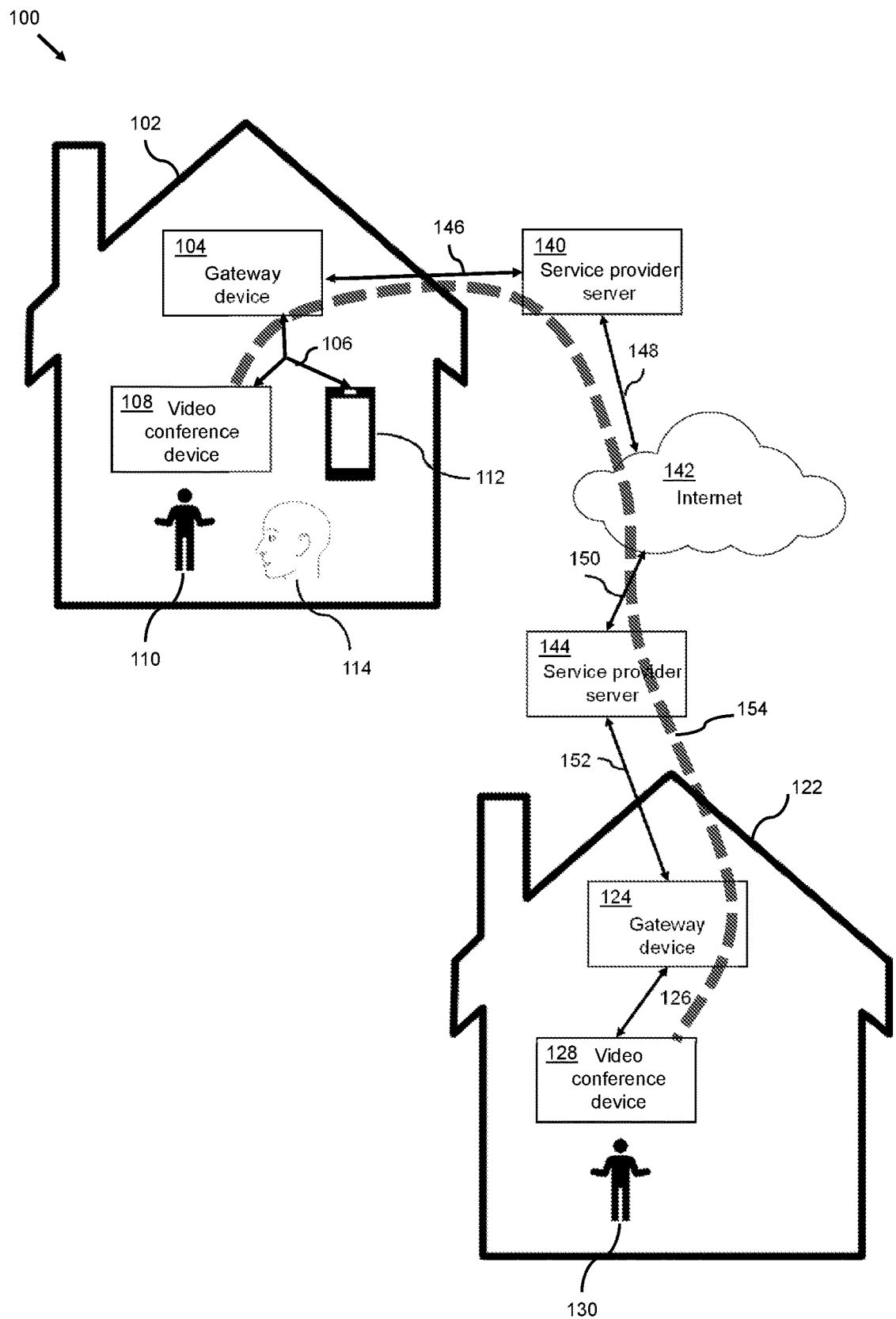
FIG. 1 illustrates a video conference system, in accordance with aspects of the present invention.

As healthcare costs continue to increase, there is an increasing desire with aging adults to stay in place (in home) and be taken care of. While there are many individual technologies to address niche problems, given the rapid rise of connectivity technologies and the use of artificial intelligence techniques for predictive and analytical methods, a more robust, cloud-based approach that accommodates multiple-modes of sensory data to determine and assist well-being of individual is needed.

There are many devices in the market today that behave as point solutions for specific monitoring of aspects of well-being. Many of these devices come with easy-to-use mobile applications and also a cloud-based offering for access to this data. Some examples include wireless-enabled diagnostic devices, for example Bluetooth-enabled pulse Oximeter. New technologies such as Wi-Fi motion detection are being proposed for deriving 'fall-detection', and advanced face recognition and image-processing techniques using smart cameras. All these bewildering set of choices and non-interoperable systems makes it difficult for ubiquitous adoption of the solutions. In addition, it makes it increasingly difficult for a caregiver, whether a near and dear or a professional caregiver, since there are multiple problems that need to be addressed.

Further, telemedicine, or virtual doctor visits, are increasingly popular especially in situations where epidemics or sheer distances prevent in-person visits. A typical virtual doctor visit involves a doctor in one location holding a video conference with a caregiver and patient at another location. The caregiver may be using a personal computer, smart phone, or tablet to establish the video conference; furthermore, the caregiver is probably using that device's camera to converse with the doctor. A problem arises when the caregiver needs to train the camera on the patient, perhaps to show a skin rash, enlarged tonsils, or other conditions, while simultaneously trying to maintain a dialog with the doctor.

Some existing video conference solutions allow for multiple devices to join a video conference, but these may not adequately address security and privacy considerations needed for telemedicine. In addition, the doctor is still reliant on verbally instructing the caregiver to position the camera relative to the patient and to manipulate the camera's settings according to the doctor's wishes.

What is needed is a system and method for controlling an authorized device's camera and light settings during a virtual doctor visit.

A system and method in accordance with the present disclosure allows the control of an authorized device's camera and light settings during a virtual doctor visit.

A proposed solution to the problems discussed above in accordance with aspects of the present disclosure includes: a mesh of "data connectivity hubs" that can work together as a virtual 'connectivity hub' to communicate with the diagnostic devices, sensors and cameras; while the mesh of hubs wirelessly connects directly to an external network portal, e.g., a gateway connecting to the Internet, relying on an external data connection, one option is to have at least of the hubs have an optional cellular backup that does not rely on an Internet Wi-Fi connection in the home; a method to securely 'pair' an instance of a diagnostic device (or sensor, or camera), with the 'hub', to establish a secure association; a method to securely communicate diagnostic data to a cloud-based aggregation portal; a cloud-based aggregation portal that would securely gather the data for analysis in a coordinated manner, with all the data associated with a given home be available to a caregiver; and mobile application to allow the stakeholders to be able to access data. A novel aspect of the present disclosure is that the application view is not just intended for the aging person, but someone near/dear. The type of information that will be presented will depend on who the stakeholder is. The aging person, the professional caregiver, the near/dear may each have potentially different views of the status.

The concept of an Internet of Things ("IoT") hub is an existing concept, and there are many examples. However, aspects of the present disclosure allow for a multitude of such hubs, disaggregating the following functions from specific devices: sensing functions and data transmission to a connected collection hub (or hubs). In non-limiting example embodiments, a sensing function may be performed with a distinct sensing device, non-limiting examples of which included: sensing oxygen saturation, as done by a pulse oximeter; image capture, as is usually done with a camera; sound capture (voice, lung sounds, heart sounds), using microphones; motion detection, as is captured by IR based motion sensors or Wi-Fi based motion sensing; blood-pressure sensing, using blood pressure meters; and temperature sensing, using thermometers. Data transmission to a connected collection hub (or hubs) involves the aspect of the sensing function to transmit the 'sensed' data to a collection device—or a collection hub. A collection hub may be a separate device such as an IoT hub that operates in accordance with the required protocols to interface with the diagnostic devices.

Aspects of the present disclosure include device articulations that have combinations of sensing functions and data transmission to a connected collection hub (or hubs). Non-limiting example of such device articulations include: a single unit that includes a camera, a far field voice ("FFV") microphone, a BLE sensor, a collection unit that may also serve to securely transmit the data over a Wi-Fi connection; a plurality of device articulations in a home, with disparate functionality, as long as amongst all the devices, the sensing, collection and transmission are accomplished; specifically, for diagnostic/sensing devices to be able to connect to any available collection hub (to improve resilience) even in the event that one of the collection hubs is temporarily not available; for the collection hubs to be able to store the data for some configurable period in case the (secure) communication via the Internet is not available; and a plurality of the collection hubs to act in a mesh network to provide resilient support to a bevy of diagnostic devices, such that the diagnostic devices always will have a high-probability of reaching one of the diagnostic hubs.

A situation may often be encountered wherein the room/ home, where the wellbeing-monitoring solution is installed, does not have any access or good wireless access to Internet, for example via Wi-Fi. In such a case, use of a cellular backup or even as the main backhaul channel for Internet access might be critical. To accommodate that, aspects of the present disclosure include a system where at least one of the collection hubs is equipped with a cellular, e.g., 4G/5G LTE, solution to securely access the Internet.

Aspects of the present disclosure additionally include one or more methods to securely associate (pairing) of the diagnostic device with the collection hub. This association may be performed the first time through registering the diagnostic device using a mobile application with a secure association to the collection hub. Once done, the association is maintained in an external server or cloud. Should the diagnostic device accidentally (or otherwise) move from one home to another, then an alert notification may be provided, for attention to be drawn to a caregiver to make sure that there is no real issue.

Aspects of the present disclosure additionally include a secure method that reliably and securely transmits the collected diagnostic data as well as other communications to an external server-based (cloud-based) portal. While there are many conventional secure protocols, an aspect of the present disclosure however additionally assures that the certificates upon which the protocols are based are securely handled at an additional level of hierarchy, so that the opportunity of data theft compromise during transmission to the cloud-portal and for internal consumption within the cloud portal is eliminated.

Aspects of the present disclosure additionally include an external server, e.g., cloud-based server, would aggregate the data collection, and also provide information to various stakeholders with appropriate privileges.

In accordance with aspects of the present disclosure, a device is capable of performing Internet video conferencing (the ability to connect to another person and see and hear them via a video monitor and speaker, as well as a video camera and microphone to capture the local video and audio). Non-limiting examples of such a device include a settop box, laptop, tablet, a smart phone, etc., and the device may be used to perform virtual doctor visits with a doctor remotely. The device may additionally connect to medical devices via a transport mechanism, e.g., any known wired or wireless protocol, and have the ability to read the medical readings off the device. Non-limiting examples of such medical devices include blood pressure cuffs, pulse oximeters, thermometers, etc.

In accordance with aspects of the present disclosure, if the doctor wants the patient to obtain the readings from the medical device, the patient may first attach the device to themselves, start obtaining the biometric data, and the readings would then be embedded into the video stream directly to the doctor. Accordingly, the video conferencing device would take the live readings from the medical device, and layer it into the video stream being sent to the doctor in a viewable format. In a non-limiting example embodiment, the live readings may be provided in the corner of the doctor's video screen. This would ensure the medical data is secure, since it is now a part of the video data being sent to the doctor, and the doctor's visit already must be secure via regulated compliances, e.g. the Health Insurance Portability and Accountability Act (HIPAA) in the of the United States. It also give the doctor real-time readings directly from the patient.

It should be noted that in some embodiments, the patient would also see the readings in their own local video monitor as well.

Still further, in some embodiments, the medical data may be encoded in some metadata also used by the video conferencing stream, as opposed to only encoding the reading directly into the video stream itself.

In accordance with a non-limiting example embodiment of the present disclosure, a wireless device is used with a first video conference device and a second video conference device connected in a video conference through a secure communications channel over a WAN. The wireless device can change its camera magnification and lighting settings in response to control signals transmitted by the second video conference device.

An example system and method for controlling an authorized device's camera and light settings during a virtual doctor visit in accordance with aspects of the present invention will now be described in greater detail with reference to FIGS. 1-6.

FIG. 1 illustrates a video conference system 100, in accordance with aspects of the present invention.

As shown in the figure, system 100 includes gateway devices 104 and 124, video conference devices 108 and 128, users 110 and 130, a wireless device 112, and an item 114. Gateway device 104, video conference device 108, user 110, wireless device 112, and item 114 are positioned in location 102; gateway device 124, video conference device 128, and user 130 are positioned in location 122. A communications channel 106 connects gateway device 104, video conference device 108, and wireless device 112. A communications channel 126 connects gateway device 124 and video conference device 108. Gateway device 104 connects to an Internet 142 through a service provider server 140 using communications channels 146 and 148, while gateway device 124 connects to Internet 142 through a service provider server 144 using communications channels 150 and 152, and altogether constitute a WAN. A secure communications channel 154 is established between wireless device 112 and gateway devices 104 and 124, using gateway devices 104 and 124, service providers 140 and 144, and Internet 142 over communications channels 106, 146, 148, 150, 152, and 126.

Gateway devices 104 and 124, also referred to as gateways, residential gateways, or RG, are electronic device that are located so as to establish local area networks (LANs) at locations 102 and 122. Locations 102 and 122 can include residential dwellings, offices, or any other business space of users 110 and 130. The terms home, office, and premises may be used synonymously herein.

Gateway devices 104 and 124 may be any devices or systems that are operable to allow data to flow from one discrete device or network to another. Gateway devices 104 and 124 may perform such functions as web acceleration and HTTP compression, flow control, encryption, redundancy switchovers, traffic restriction policy enforcement, data compression, TCP performance enhancements (e.g., TCP spoofing), quality of service functions (e.g., classification, prioritization, differentiation, random early detection, TCP/UDP flow control), bandwidth usage policing, dynamic load balancing, address translation, and routing. In this non-limiting example, Gateway devices 104 and 124 may be routers, gateways, extenders, or mesh network devices.

Video conference devices 108 and 128 are any devices or methods that are able to establish a video conference wherein video and audio data from video conference device 108 is presented on video conference device 128 and video and audio data from video conference device 128 is presented on video conference device 108. In this non-limiting example, video conference devices 108 and 128 may be smart phones, tablets, personal computers, TV set-top boxes, videogame consoles, or smart media devices.

Wireless device 112 is any device or method containing a camera, light, and network interface that is able to transmit images to video conference device 108. In this non-limiting example, wireless device 112 may be an action camera, smart phone, tablet, personal computer, TV set-top box, videogame console, or smart media device.

Service provider servers 140 and 144 include head-end equipment such as server computers (e.g., automatic configuration server ACS, cable modem termination system CMTS) that enable service provider servers 140 and 144, such as cable television providers, satellite television providers, internet service providers, or multiple-systems operators (MSOs), to provide content such as audio/video content and/or internet service through communications channels 146 and 152 utilizing physical media/wiring such as coaxial networks, optical fiber networks, or DSL; or wireless infrastructure such as satellites, terrestrial antennas, or any combination of these examples or their equivalents.

Communications channels 106, 146, 148, 150, 152, and 126 are any devices or methods that facilitate communications between devices or networks. In this non-limiting example, communications channels 106 and 126 are Wi-Fi or Bluetooth channels. The term "Wi-Fi" as used herein may be considered to refer to any of Wi-Fi 4, 5, 6, 6E, or any variation thereof. The term "Bluetooth" as used herein may be considered to refer to Classic Bluetooth, Bluetooth high speed, or Bluetooth Low Energy (BLE) protocols, or any variation thereof. Communications channels 106, 146, 148, 150, 152, and 126 may include physical media or wiring, such as coaxial cable, optical fiber, or digital subscriber line (DSL); or wireless links, such as LTE, satellite, or terrestrial radio links; or a combination of any of these examples or their equivalents. The data communicated on such networks can be implemented using a variety of protocols on a network such as a WAN, a virtual private network (VPN), a metropolitan area network (MAN), a system area network (SAN), a DOCSIS network, a fiber optics network (including fiber-to-the-home, fiber-to-the-X, or hybrid fiber-coax), a digital subscriber line (DSL), a public switched data network (PSDN), a global Telex network, or a 2G, 3G, 4G or 5G, for example. Though communications channels 106, 146, 148, 150, 152, and 126 are shown as single links, it is contemplated that communications channels 106, 146, 148, 150, 152, and 126 may contain multiple links and devices including access points, routers, gateways, and servers.

User 110 is a person using video conference device 108 at location 102. In this non-limiting example, user 110 is a parent and item 114 is a child. User 130 is a person using video conference device 128 at location 122. In this non-limiting example, user 130 is a doctor.

In normal operation, video conference device 108 establishes secure communications channel 154 to video conference device 128. User 130 conducts a virtual doctor visit with user 110 using video conference devices 108 and 128 over secure communications channel 154. For purposes of discussion, suppose that during the virtual doctor session user 130 desires to examine item 114 more closely. User 110 establishes a secure connection between wireless device 112 and video conference device 108, which adds wireless device 112 to secure communications channel 154. User 110 positions wireless device 112 in a manner that user 130 can examine item 114. User 130 can control camera magnification and lighting on wireless device 112 by transmitting control signals from video conference device 128. In this manner, user 110 and user 130 can continue their existing video conference on video conference devices 108 and 128 while using wireless device 112 to provide images of item 114.

FIG. 1 illustrates a video conference being conducted on video conference system 100. Components of video conference system 100 will now be discussed in greater detail with reference to FIG. 2.

Figure 2:
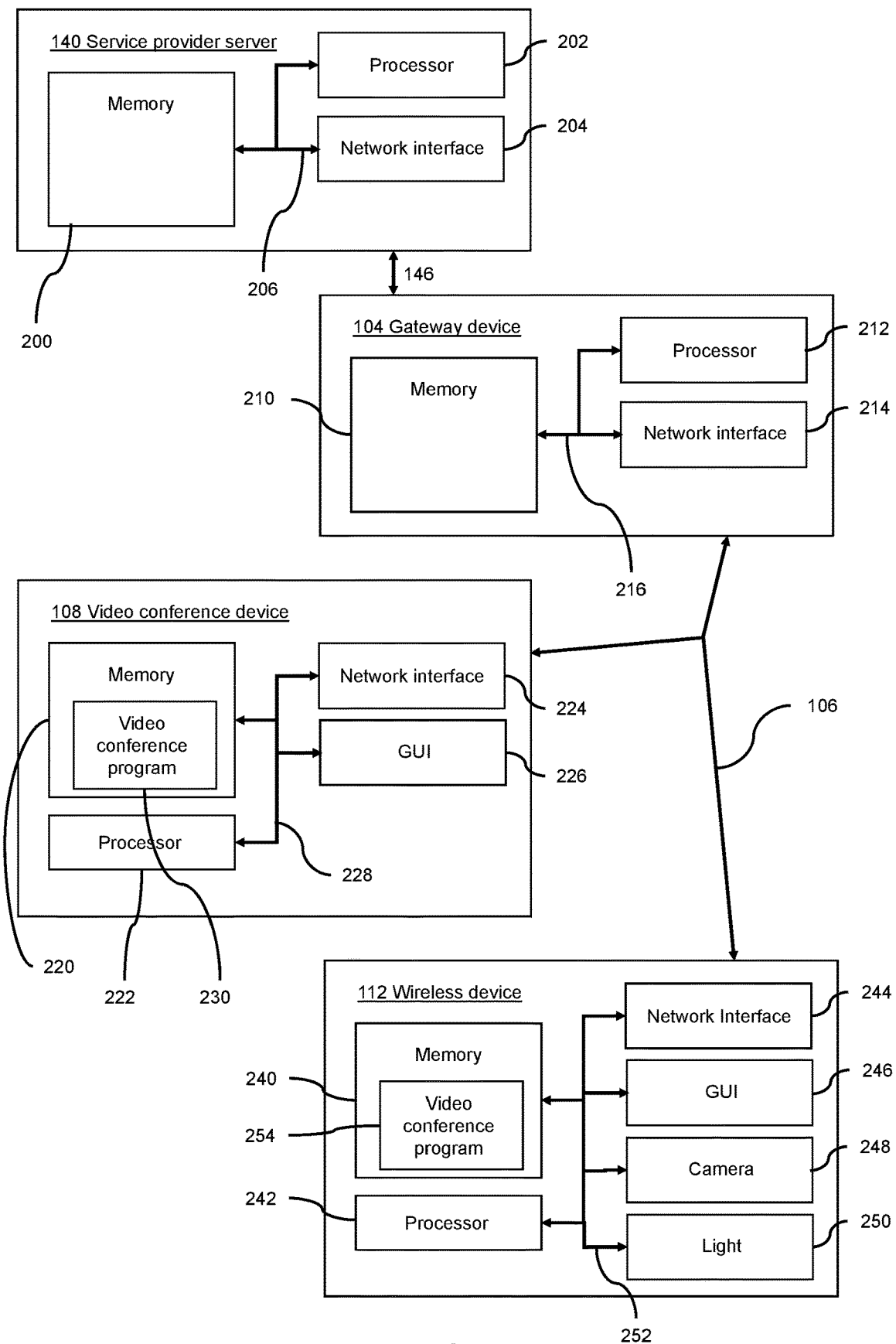
FIG. 2 illustrates a service provider server, a gateway device, a video conference device, and a wireless device, in accordance with aspects of the present invention.

FIG. 2 illustrates an exploded view of service provider server 140, gateway device 104, video conference device 108, and wireless device 112, in accordance with aspects of the present invention.

As shown in the figure, service provider server 140 contains a memory 200, a processor 202, and a network interface 204. Memory 200, processor 202, and network interface 204 are connected by a bus 206. Gateway device 104 contains a memory 210, a processor 212, and a network interface 214. Memory 210, processor 212, and network interface 214 are connected by a bus 216. Video conference device 108 contains a memory 220, a processor 222, a network interface 224, and a graphical user interface (GUI) 226. Memory 220, processor 222, network interface 224, and GUI 226 are connected by a bus 228. A video conference program 230 is contained in memory 220 and is executed by processor 222. Wireless device 112 contains a memory 240, a processor 242, a network interface 244, a GUI 246, a camera 248, and a light 250. Memory 240, processor 242, network interface 244, GUI 246, camera 248, and light 250 are connected by bus 252. A video conference program 254 is contained in memory 240 and is executed by processor 242.

Though only service provider server 140, gateway device 104, and video conference device 108 are shown in FIG. 2, it is contemplated that service provider server 144 is substantially similar to service provider server 140, that gateway device 124 is substantially similar to gateway device 104, and that video conference device 128 is substantially similar to video conference device 108.

Processors 202, 212, 222, and 242 are any devices or methods capable of controlling general operations of devices 140, 104, 108, and 112 respectively, and include, but are not limited to, central processing units (CPUs), hardware microprocessors, single-core processors, multi-core processors, field-programmable gate arrays (FPGAs), microcontrollers, application-specific integrated circuits (ASICs), digital signal processors (DSPs), or other similar processing devices capable of executing any type of instructions, algorithms, or software for controlling the operation and functions of devices 140, 104, 108, and 112.

Memories 200, 210, 220, and 240 are any devices or methods capable of storing data and instructions used by devices 140, 104, 108, and 112 respectively, and include, but are not limited to, random-access memory (RAM), dynamic random-access memory (DRAM), hard drives, solid-state drives, read-only memory (ROM), erasable programmable read-only memory (EPROM), electrically erasable programmable read-only memory (EEPROM), flash memory, embedded memory blocks in FPGAs, or any other various layers of memory hierarchy.

Network interfaces 204, 214, 224, and 244 are any devices or methods used to establish and maintain communications channels 146 and 106. Network interfaces 214, 224, and 244 may include one or more antennas and communicate wirelessly via one or more of the 2.4 GHz band, the 5 GHz band, the 6 GHz band, and the 60 GHz band, or at the appropriate band and bandwidth to implement any IEEE 802.11 Wi-Fi protocols, such as the Wi-Fi 4, 5, 6, or 6E protocols. Devices 104, 108, and 112 can also be equipped with radio transceivers or wireless communication circuits to implement wireless connections in accordance with any Bluetooth protocols, Bluetooth Low Energy (BLE), or other short-range protocols that operate in accordance with a wireless technology standard for exchanging data over short distances using any licensed or unlicensed band such as the CBRS band, 2.4 GHz bands, 5 GHz bands, 6 GHz bands, or 60 GHz bands, RF4CE protocol, ZigBee protocol, Z-Wave protocol, or IEEE 802.15.4 protocol.

GUIs 226 and 246 are any devices or methods capable of presenting information and accepting user inputs on devices 108 and 112 respectively, and include, but are not limited to, liquid crystal displays (LCDs), thin film transistor (TFT) displays, light-emitting diode (LED) displays, or other similar display devices, including display devices having touch screen capabilities so as to allow interaction between user 110 (as shown in FIG. 1) and devices 108 and 112.

Camera 248 is any device or method that forms an image of item 114 (as shown in FIG. 1). In this non-limiting example, the image magnification, or "zoom," of item 114 can be varied. In some embodiments, as will be described in greater detail below, camera 248 may be configured to configured to: image item 114 in a first magnification; output first image data of item 114 based on the first magnification; change the magnification; image item 114 in a second magnification; and output second image data of item 114 based on the second magnification.

Light 250 is any device or method that illuminates item 114. In this non-limiting example, the intensity and color of light 250 can be varied.

In this example, processor 242, memory 240, network interface 244, GUI 246, camera 248, and light 250 are illustrated as individual components of wireless device 112. However, in some embodiments, at least two of processor 242, memory 240, network interface 244, GUI 246, camera 248, and light 250 may be combined as a unitary device. Further, in some embodiments, at least one of processor 242, memory 240, and network interface 244 may be implemented as a computer having non-transitory computer-readable media for carrying or having computer-executable instructions or data structures stored thereon. Such non-transitory computer-readable recording medium refers to any computer program product, apparatus or device, such as a magnetic disk, optical disk, solid-state storage device, memory, programmable logic devices (PLDs), DRAM, RAM, ROM, EEPROM, CD-ROM or other optical disk storage, magnetic disk storage or other magnetic storage devices, or any other medium that can be used to carry or store desired computer-readable program code in the form of instructions or data structures and that can be accessed by a general-purpose or special-purpose computer, or a general-purpose or special-purpose processor. Disk or disc, as used herein, includes compact disc (CD), laser disc, optical disc, digital versatile disc (DVD), floppy disk and Blu-ray disc. Combinations of the above are also included within the scope of computer-readable media. For information transferred or provided over a network or another communications connection (either hardwired, wireless, or a combination of hardwired or wireless) to a computer, the computer may properly view the connection as a computer-readable medium. Thus, any such connection may be properly termed a computer-readable medium. Combinations of the above should also be included within the scope of computer-readable media.

Example tangible computer-readable media may be coupled to processor 242 such that the processor may read information from, and write information to the tangible computer-readable media. In the alternative, the tangible computer-readable media may be integral to processor 242. Processor 242 and the tangible computer-readable media may reside in an integrated circuit (IC), an ASIC, or large scale integrated circuit (LSI), system LSI, super LSI, or ultra LSI components that perform a part or all of the functions described herein. In the alternative, processor 242 and the tangible computer-readable media may reside as discrete components.

Example tangible computer-readable media may be also coupled to systems, non-limiting examples of which include a computer system/server, which is operational with numerous other general purpose or special purpose computing system environments or configurations. Examples of well-known computing systems, environments, and/or configurations that may be suitable for use with computer system/server include, but are not limited to, personal computer systems, server computer systems, thin clients, thick clients, handheld or laptop devices, multiprocessor systems, microprocessor-based systems, set-top boxes, programmable consumer electronics, network PCs, minicomputer systems, mainframe computer systems, and distributed cloud computing environments that include any of the above systems or devices, and the like.

Such a computer system/server may be described in the general context of computer system-executable instructions, such as program modules, being executed by a computer system. Generally, program modules may include routines, programs, objects, components, logic, data structures, and so on that perform particular tasks or implement particular abstract data types. Further, such a computer system/server may be practiced in distributed cloud computing environments where tasks are performed by remote processing devices that are linked through a communications network. In a distributed cloud computing environment, program modules may be located in both local and remote computer system storage media including memory storage devices.

Similar structures and combinations may exist for components of service provider server 140, gateway device 104, and video conference device 108.

Bus 252 is any device or method that provides data communications between processor 242, memory 240, network interface 244, GUI 246, camera 248, and light 250 of wireless device 112. Bus 252 can be one or more of any of several types of bus structures, including a memory bus or a memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus. Similar relationships define buses 206, 216, and 228 contained in service provider server 140, gateway device 104, and video conference device 108, respectively.

Video conference program 254 establishes and maintains the video conference session on wireless device 112. Video conference program 254, having a set (at least one) of program modules, may be stored in memory 240 by way of example, and not limitation, as well as an operating system, one or more application programs, other program modules, and program data. Each of the operating system, one or more application programs, other program modules, and program data or some combination thereof, may include an implementation of a networking environment. The program modules generally carry out the functions and/or methodologies of various embodiments of the application as described herein.

Further, in some embodiments, as will be described in greater detail below, video conference program 254 includes instructions, that when executed by processor 242, enable wireless device 112 to: transmit a video conference request to video conference device 108; receive a video conference invitation from video conference device 108; establish a communication channel with video conference device 108; transmit image data to video conference device 128; receive a magnification control signal from video conference device 128; instruct camera 248 to change the magnification based on the magnification control signal; and transmit second image data to video conference device 128.

Further, in some embodiments, as will be described in greater detail below, video conference program 254 includes instructions, that when executed by processor 242, enable wireless device 112 additionally to: instruct light 250 to provide a first illumination; receive a lighting control signal from video conference device 128; and instruct light 250 to provide a second illumination based on the lighting control signal.

Still further, in some embodiments, as will be described in greater detail below, video conference program 254 includes instructions, that when executed by processor 242, enable wireless device 112 to: receive credentials from video conference device 108; establish a communication channel with first video conference device 108 based on the received credentials; transmit first image data to video conference device 108; receive a magnification control signal from video conference device 108; instruct camera 248 to change the magnification based on the magnification control signal; and transmit second image data to video conference device 108.

Video conference program 230 establishes and maintains the video conference session on video conference device 108. Video conference program 230, having a set (at least one) of program modules, may be stored in memory 220.

FIGS. 1-2 describe a video conference system containing devices and users at different locations. A method of operating the video conference and controlling connected devices will now be discussed with reference to FIG. 3.

Figure 3:
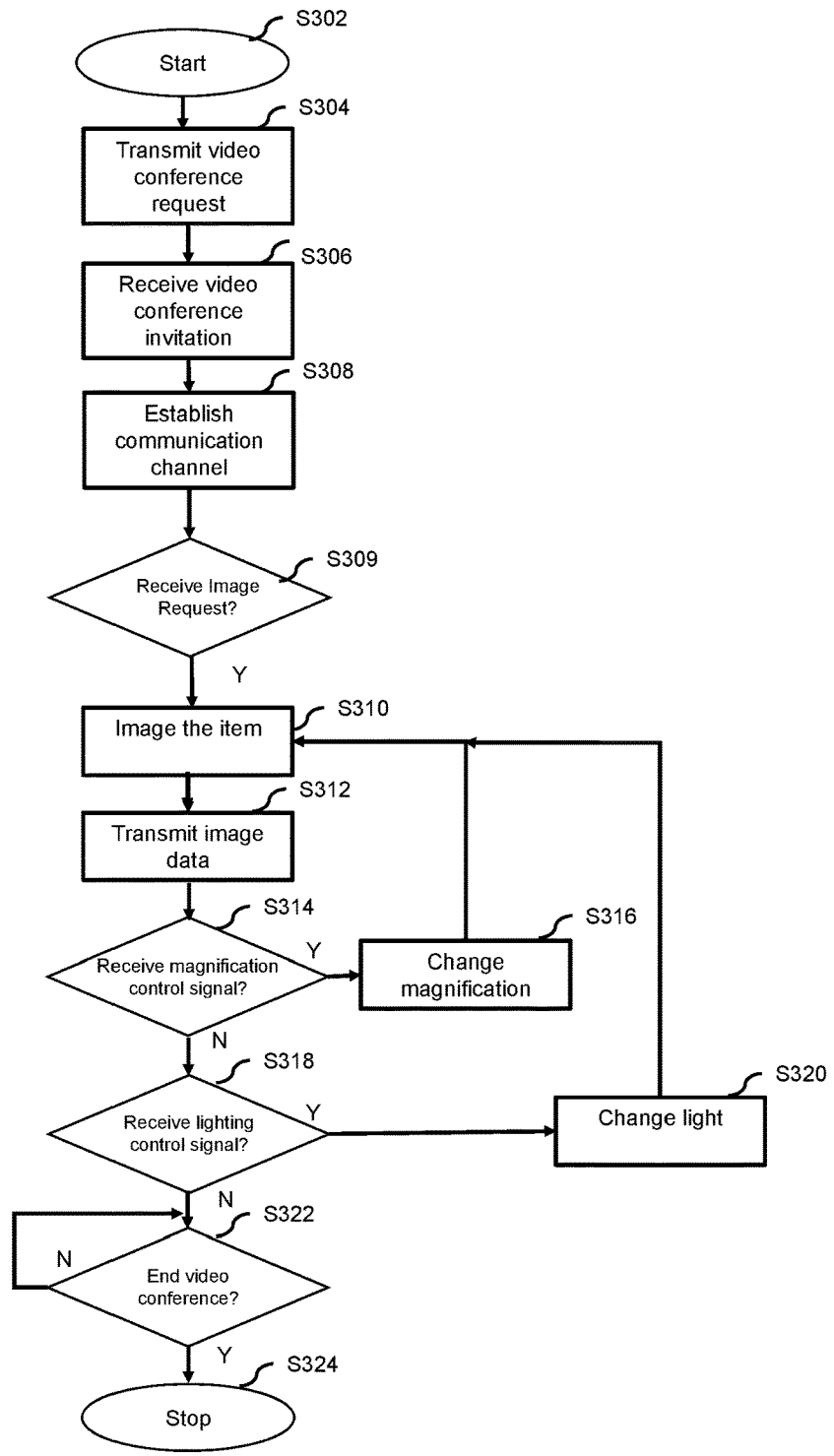
FIG. 3 illustrates a method of controlling image magnification and lighting, in accordance with aspects of the present invention.

FIG. 3 illustrates an algorithm 300 to be executed by a processor for controlling image magnification and lighting, in accordance with aspects of the present invention.

As shown in the figure, algorithm 300 starts (S302) and a video conference request is transmitted (S304). For purposes of discussion and referring to FIG. 2, suppose user 110 wants to add wireless device 112 into the virtual doctor session. User 110 initiates an authorization procedure using GUI 246 on wireless device 112. Video conference program 254 running on processor 242 of wireless device 112 transmits the video conference request to video conference device 108 over communications channel 106. Video conference device 108 validates the video conference request then transmits a video conference invitation to wireless device 112.

For example, for purposes of discussion, let wireless device 112 be a smart phone. In some non-limiting example embodiments, a button prompt may be provided on the screen that reads "Join Video Conference." Upon pressing the button prompt, wireless device 112 may transmit the video conference request to video conference device 108.

Returning to FIG. 3, the video conference invitation is received (S306) and a video conference communications channel is established (S308). In operation and referring to FIG. 2, wireless device 112 receives the video conference invitation from video conference device 108. For example, for purposes of discussion, continuing with the discussion above wherein wireless device 112 is a smart phone, in some non-limiting example embodiments, a new button prompt reading "Join Video Conference?" may be provided to the screen. This second button prompt verifies that user 110 still desires to have wireless device 112 join the video conference.

Video conference program 254 and video conference program 230 then execute instructions to add wireless device 112 to secure communications channel 154 (as shown in FIG. 1). The virtual doctor session is then able to transmit data generated by any device linked by secure communications channel 154. For example, when user 110 presses the button prompt "Join Video Conference?," wireless device 112 immediately finds the existing video conference session by way of the invitation from video conference device 108. Wireless device 112 then sets up a secure camera stream. In some embodiments, the camera stream is only one way, from wireless device 112 to video conference device 128, as there may not be a need to have the doctor's video to be supplied to wireless device 112.

Returning to FIG. 3, after the video conference communications channel is established (S308), it is determined whether an image request is received (S309). For example, if the doctor would like to have access to an additional video source, wherein he can control aspects of the video source, the doctor may ask the parent to enable their phone to be used as a secondary imaging device, and to let the doctor control aspects of the camera on the phone. In this way, the doctor may, for example, increase/decrease the zoom as needed and change the lighting.

In non-limiting example embodiments, for example as shown in FIG. 1, the doctor may initiate the process of inviting, accessing and then controlling the phone of the parent in order to more easily view the child. More particularly, video conference device 108 would send a device control request to video conference device 124.

If video conference device 128 receives the device control request, then it is determined that an image request is received (Y at S309). However, if video conference device 128 does not receive the device control request, then it is determined that an image request is not received (N at S309).

Returning to FIG. 3, if an image request is received (Y at S309), then the item is imaged (S310). As shown in FIG. 2, processor 222 of video conference device 108 would execute instructions in video conference program 230 to send the device control request to wireless device 112. Upon receiving the device control request, processor 242 of wireless device 112 would execute instructions in video conference program 254 to enable camera 248. In operation and referring to FIGS. 1 and 2, video conference program 254 instructs camera 248 to image item 114. In some embodiments, the image may be a still picture, whereas in other embodiments, the image may be a video.

Returning to FIG. 3, image data is transmitted (S312). In operation and referring to FIGS. 1 and 2, wireless device 112 transmits image data to video conference device 108 and eventually to video conference device 128 over secure communications channel 154.

Returning to FIG. 3, it is determined whether an image magnification control signal is received (S314). If an image magnification control signal is received (Y on S314) then image magnification is changed (S316). For example, referring to FIGS. 1 and 2, user 130 may desire to have a closer look at item 114. Instead of verbally instructing user 110 to reposition wireless device 112, user 130 can send a command through video conference device 128 to change magnification. Video conference device 128 generates a magnification control signal, which is transmitted through secure communications channel 154. Wireless device 112 receives the magnification control signal, and processor 242 instructs camera 248 to change its magnification level. The change in image magnification will now be discussed with reference to FIGS. 4A-B.

Figure 4A:
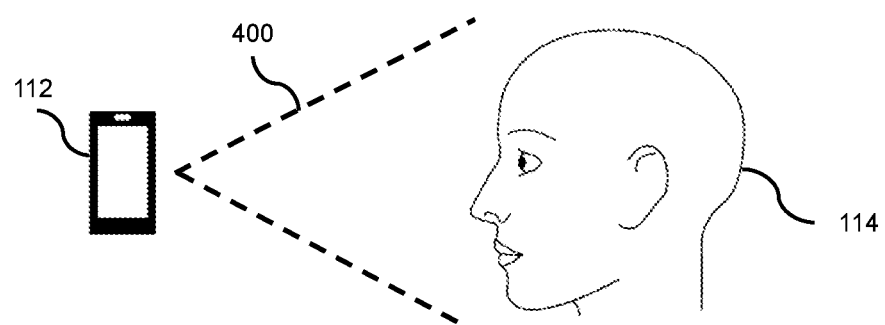
FIGS. 4A-B illustrate changes of image magnification, in accordance with aspects of the present invention.
Figure 4B:
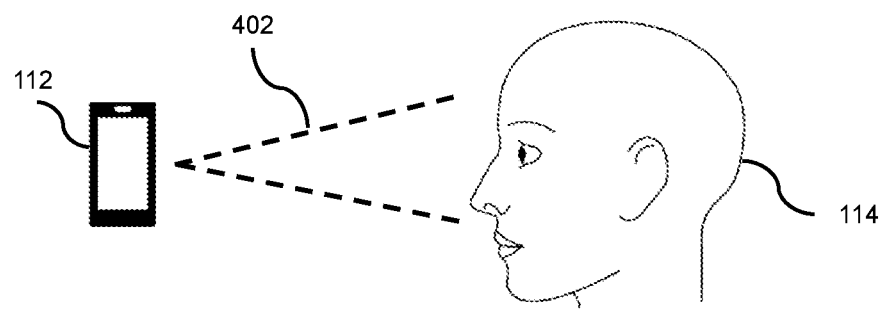

FIGS. 4A-B illustrate image magnifications 400 and 402, in accordance with aspects of the present invention.

As shown in FIG. 4A, wireless device 112 images item 114 at image magnification 400. As shown in FIG. 4B, wireless device 112 images item 114 at a new image magnification 402 after receiving the magnification control signal. In this non-limiting example, image magnification 402 is of a narrower viewing angle, or a higher magnification level, than image magnification 400. In other embodiments, image magnification 402 may be of a wider viewing angle, or lower magnification level, than image magnification 400.

Returning to FIG. 3, the item is re-imaged (S310) and a new image is transmitted (S312). For example, referring to FIGS. 1 and 2, camera 248 records a new image of item 114 and transmits the image data to video conference devices 108 and 128 over secure communications channel 154.

Returning to FIG. 3, if there is no magnification control signal (N on S314) then it is determined whether a lighting control signal is received (S318). If a lighting control signal is received (Y on S318) then lighting is changed (S320). For example, referring to FIGS. 1 and 2, user 130 may find the image of item 114 to be too dark. Instead of verbally instructing user 110 to turn on room lights, user 130 can send a command through video conference device 128 to turn on light 250 on wireless device 112. Video conference device 128 generates a lighting control signal, which is transmitted through secure communications channel 154. Wireless device 112 receives the lighting control signal, and processor 242 instructs light 250 to change its color or intensity. The change in lighting will now be discussed with reference to FIGS. 5A-B.

Figure 5A:
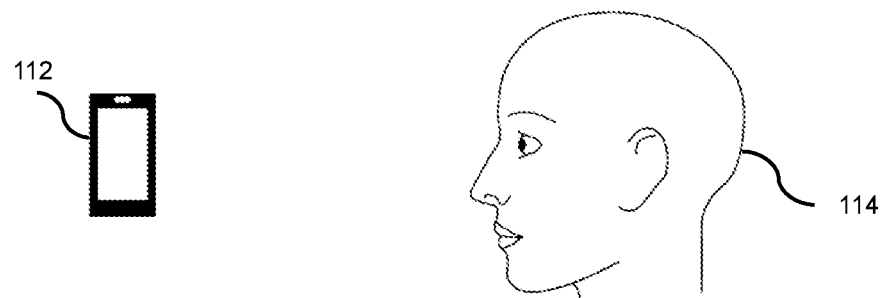
FIGS. 5A-B illustrate changes of lighting, in accordance with aspects of the present invention.
Figure 5B:
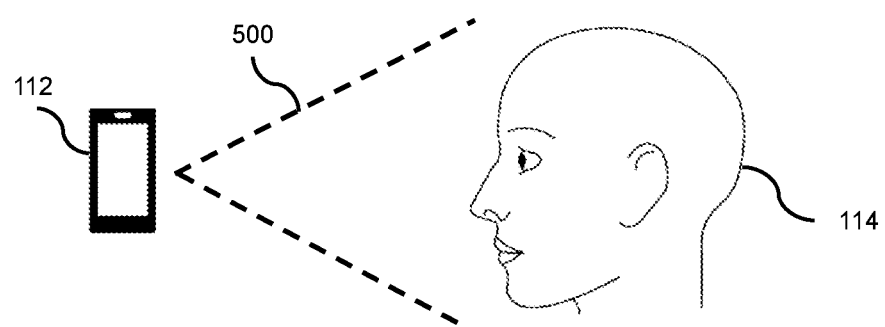

FIGS. 5A-B illustrate changes in lighting, in accordance with aspects of the present invention.

As shown in FIG. 5A, wireless device 112 images item 114 with no supplemental lighting from wireless device 112. As shown in FIG. 5B, wireless device 112 images item 114 with lighting 500 that is created by light 250 in response to the lighting control signal initiated by user 130 on video conference device 128. In this non-limiting example, light 250 is switched on from an "off" state. In other embodiments, user 130 may vary intensity or color level of light 250.

Returning to FIG. 3, the item is re-imaged (S310) and a new image is transmitted (S312). For example, referring to FIGS. 1 and 2, camera 248 records a new image of item 114 and transmits the image data to video conference devices 108 and 128 over secure communications channel 154.

If no lighting control signal is received (N on S318) then it is determined whether the video conference is ended (S322). The video conference continues (N on S322) until the video conference is terminated (Y on 322), then algorithm 300 stops (S324).

In some embodiments, returning to FIG. 1, user 130 may cause video conference device 128 to transmit a close camera instruction to wireless device 112 over secure communications channel 154. For example, as shown in FIG. 2, upon receiving the close camera instruction from video conference device 128, processor 222 of video conference device 108 may execute instructions in video conference program 230 to instruct network interface 224 to transmit the close camera instruction to wireless device 112. The close camera instruction may be transmitted by any know protocol for which video conference device 108 communicates with wireless device 112, non-limiting examples of which include Ethernet, Wi-Fi, and Bluetooth. Upon receiving the close camera instruction from video conference device 108, processor 242 of wireless device 112 may execute instructions in video conference program 254 to turn off camera 248. User 130 may use the close camera instruction when user 130 no longer needs to use camera 248 of wireless device 112.

In the example embodiments discussed above, user 130 is able to remotely control the lighting and magnification of wireless device 112 by way of video conference device 128. However, it should be noted that user 130 may additionally or alternatively remotely control additional features or functions of wireless device 112 by way of video conference device 128. A non-limiting example of an additional feature includes controlling a microphone on wireless device 112, for example to hear a heartbeat.

FIG. 3 illustrates algorithm 300 to be executed by a processor for controlling image magnification and lighting in a session that is initiated by wireless device 112. A similar method for a session that is initiated by video conference device 108 will now be discussed with reference to FIG. 6.

Figure 6:
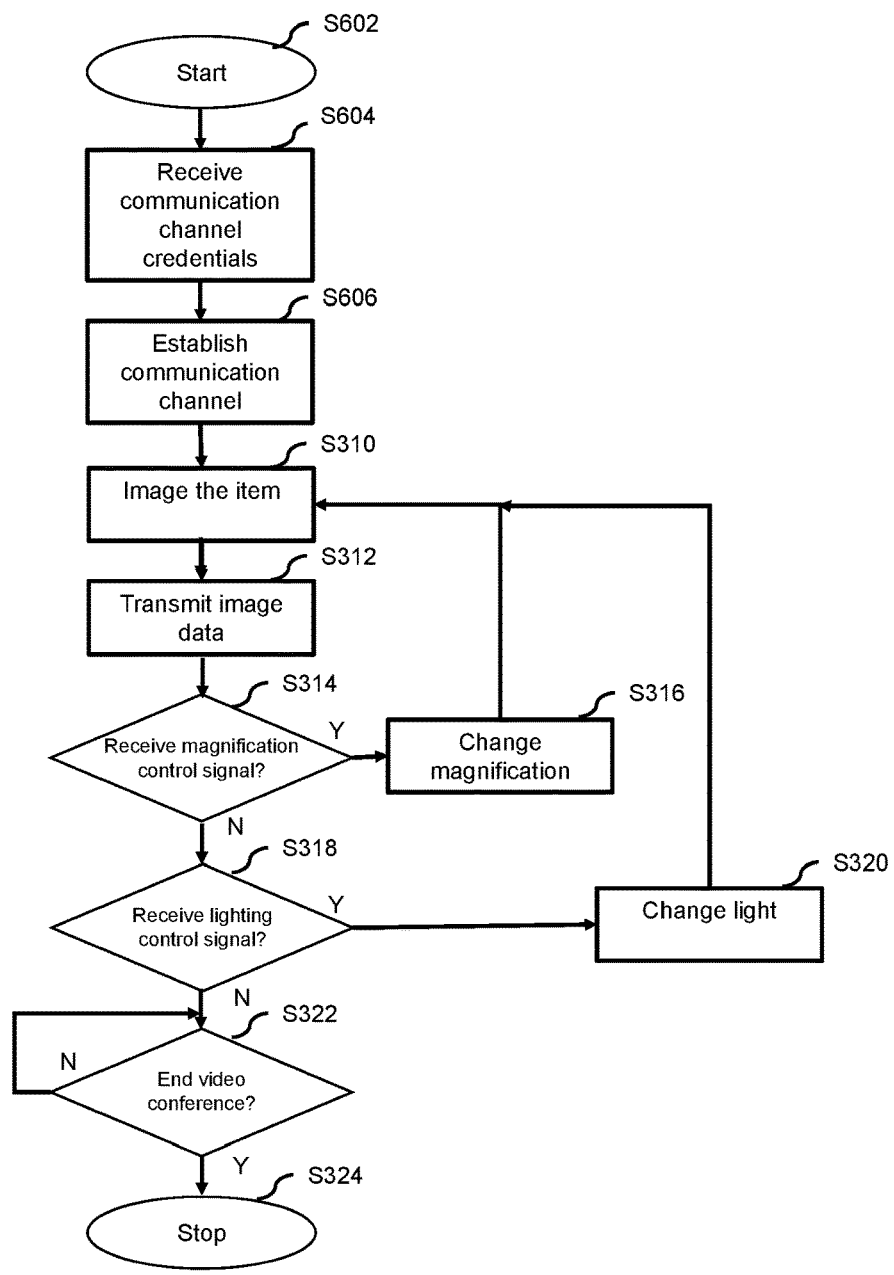
FIG. 6 illustrates a method of controlling image magnification and lighting, in accordance with aspects of the present invention.

FIG. 6 illustrates an algorithm 600 to be executed by a processor for controlling image magnification and lighting, in accordance with aspects of the present invention.

As shown in the figure, algorithm 600 starts (S602) and communications channel credentials are received (S604). For purposes of discussion and referring to FIG. 2, suppose user 110 wants to add wireless device 112 into the virtual doctor session. User 110 initiates an authorization procedure using GUI 226 of video conference device 108. Video conference program 230 running on processor 222 of video conference device 108 transmits communications channel credentials to wireless device 112 over communications channel 106.

Returning to FIG. 6, after the communication channel credentials are received (S604), a video conference communications channel is established (S606). For example, referring to FIG. 2, wireless device 112 receives communications channel credentials from video conference device 108. Video conference program 254 and video conference program 230 then execute instructions to add wireless device 112 to secure communications channel 154. The virtual doctor session is then able to transmit data generated by any device linked by secure communications channel 154.

For example, for purposes of discussion, let wireless device 112 be a smart phone. In some non-limiting example embodiments, a button prompt reading "Join Video Conference?" may be provided to the screen upon receipt of the communication channel credentials from video conference device 108.

Video conference program 254 and video conference program 230 then execute instructions to add wireless device 112 to secure communications channel 154 (as shown in FIG. 1). The virtual doctor session is then able to transmit data generated by any device linked by secure communications channel 154. For example, when user 110 presses the prompt "Join Video Conference?," wireless device 112 immediately finds the existing video conference session by way of the communication channel credentials from video conference device 108. Wireless device 112 then sets up a secure one camera stream. In some embodiments, the camera stream is only one way, from wireless device 112 to video conference device 128, as there may not be a need to have the Doctor's video supplied to wireless device 112.

Returning to FIG. 6, the item is imaged (S608). From this step onwards, algorithm 600 is identical to algorithm 300 as discussed above with reference to FIG. 3.

Telemedicine, including virtual doctor visits, is playing an increasingly greater role in the health care field. A typical telemedicine video conference solution involves a single device at a doctor's location connecting to a single device at a patient's or caregiver's location. A limitation with such a video conference is that the patient or caregiver may find it awkward, for example, to position the device's camera in a manner that allows the doctor to examine the patient more closely while maintaining a video dialog with the doctor.

In accordance with the present invention, a wireless device at the patient's location is authorized to join the secure communications channel used by the video conference being held between patient and doctor. The doctor may remotely command the patient's wireless device to change image magnification and lighting. This system and method separate diagnostic and sensing functions from data collection and transmission functions and enables the inclusion of other health-monitoring devices such as blood oxygen monitors, motion-detecting smart watches, blood pressure sensors, and thermometers in a secure and private manner during the virtual doctor visit.

The foregoing description of various preferred embodiments have been presented for purposes of illustration and description. It is not intended to be exhaustive or to limit the present disclosure to the precise forms disclosed, and obviously many modifications and variations are possible in light of the above teaching. The example embodiments, as described above, were chosen and described in order to best explain the principles of the present disclosure and its practical application to thereby enable others skilled in the art to best utilize the present disclosure in various embodiments and with various modifications as are suited to the particular use contemplated. It is intended that the scope of the present disclosure be defined by the claims appended hereto.

What is claimed is:

1. A wireless device for use with a first video conference device, a second video conference device, a wide area network ("WAN") and an item, the first video conference device and the second video conference device being configured to establish a video conference over a secure communication channel over the WAN, the first video conference device being configured to provide first video data and first audio data to the second video conference device during the video conference, the second video conference device being configured to provide second video data and second audio data to the first video conference device during the video conference, the first video conference device being additionally configured to display the second video data and to output the second audio data, the second video conference device being additionally configured to display the first video data and to output the first audio data, the first video conference device additionally being configured to transmit a video conference invitation in response to a video conference request, the video conference invitation including credentials to establish a communication channel with the first video conference device, the second video conference device being additionally configured to transmit a magnification control signal, said wireless device comprising:
    a camera configured to:
        image the item in a first magnification;
        output first image data of the item based on the first magnification;
        change the magnification;
        image the item in a second magnification; and
        output second image data of the item based on the second magnification;
    a memory; and
    a processor configured to execute instructions stored on said memory to cause said wireless device to:
        transmit the video conference request to the first video conference device;
        receive the video conference invitation;
        establish the communication channel with the first video conference device;
        transmit the first image data to the second video conference device;
        receive the magnification control signal from the second video conference device;
        instruct the camera to change the magnification based on the magnification control signal; and
        transmit the second image data to the second video conference device.

2. The wireless device of claim 1, wherein the second video conference device is additionally configured to transmit a lighting control signal, said wireless device further comprising:
    a light configured to provide a first illumination and to provide a second illumination,
    wherein said processor configured to execute instructions stored on said memory to additionally cause said wireless device to:
        instruct the light to provide the first illumination;
        receive the lighting control signal; and instruct the light to provide the second illumination based on the lighting control signal.

3. A method of using a wireless device with a first video conference device, a second video conference device, a wide area network ("WAN") and an item, the first video conference device and the second video conference device being configured to establish a video conference over a secure communication channel over the WAN, the first video conference device being configured to provide first video data and first audio data to the second video conference device during the video conference, the second video conference device being configured to provide second video data and second audio data to the first video conference device during the video conference, the first video conference device being additionally configured to display the second video data and to output the second audio data, the second video conference device being additionally configured to display the first video data and to output the first audio data, the first video conference device additionally being configured to transmit a video conference invitation in response to a video conference request, the video conference invitation including credentials to establish a communication channel with the first video conference device, the second video conference device being additionally configured to transmit a magnification control signal, said method comprising:
  imaging, via a camera, the item in a first magnification;
  outputting, via the camera, first image data of the item based on the first magnification;
  transmitting, via a processor configured to execute instructions stored on a memory, a video conference request to the first video conference device;
  receiving, via the processor, the video conference invitation;
  establishing, via the processor, the communication channel with the first video conference device;
  transmitting, via the processor, the first image data to the second video conference device;
  receiving, via the processor, the magnification control signal from the second video conference device;
  instructing, via the processor, the camera to change the magnification based on the magnification control signal;
  changing, via the camera, the magnification;
  imaging, via the camera, the item in a second magnification;
  outputting, via the camera, second image data of the item based on the second magnification; and
  transmitting, via the processor, the second image data to the second video conference device.

4. The method of claim 3, wherein the second video conference device is additionally configured to transmit a lighting control signal, said method further comprising:
  providing, via a light, a first illumination;
  receiving, via the processor, the lighting control signal; and
  instructing, via the processor, the light to provide a second illumination based on the lighting control signal.

5. A non-transitory, computer-readable media having computer-readable instructions stored thereon, the computer-readable instructions being capable of being read by a wireless device for use with a first video conference device, a second video conference device, a wide area network ("WAN") and an item, the first video conference device and the second video conference device being configured to establish a video conference over a secure communication channel over the WAN, the first video conference device being configured to provide first video data and first audio data to the second video conference device during the video conference, the second video conference device being configured to provide second video data and second audio data to the first video conference device during the video conference, the first video conference device being additionally configured to display the second video data and to output the second audio data, the second video conference device being additionally configured to display the first video data and to output the first audio data, the first video conference device additionally being configured to transmit a video conference invitation in response to a video conference request, the video conference invitation including credentials to establish a communication channel with the first video conference device, the second video conference device being additionally configured to transmit a magnification control signal, wherein the computer-readable instructions are capable of instructing the wireless device to perform the method comprising:
  imaging, via a camera, the item in a first magnification;
  outputting, via the camera, first image data of the item based on the first magnification;
  transmitting, via a processor configured to execute instructions stored on a memory, a video conference request to the first video conference device;
  receiving, via the processor, the video conference invitation;
  establishing, via the processor, the communication channel with the first video conference device;
  transmitting, via the processor, the first image data to the second video conference device;
  receiving, via the processor, the magnification control signal from the second video conference device;
  instructing, via the processor, the camera to change the magnification based on the magnification control signal;
  changing, via the camera, the magnification;
  imaging, via the camera, the item in a second magnification;
  outputting, via the camera, second image data of the item based on the second magnification; and
  transmitting, via the processor, the second image data to the second video conference device.

6. The non-transitory, computer-readable media of claim 5, wherein the second video conference device is additionally configured to transmit a lighting control signal, and wherein the computer-readable instructions are capable of instructing the wireless device to perform the method further comprising:
  providing, via a light, a first illumination;
  receiving, via the processor, the lighting control signal; and
  instructing, via the processor, the light to provide a second illumination based on the lighting control signal.

7. A wireless device for use with a first video conference device, a second video conference device, a wide area network ("WAN") and an item, the first video conference device and the second video conference device being configured to establish a video conference over a secure communication channel over the WAN, the first video conference device being configured to provide first video data and first audio data to the second video conference device during the video conference, the second video conference device being configured to provide second video data and second audio data to the first video conference device during the video conference, the first video conference device being additionally configured to display the second video data and to output the second audio data, the second video conference device being additionally configured to display the first video data and to output the first audio data, the first video conference device additionally being configured to transmit credentials to establish a communication channel with said wireless device, the second video conference device being additionally configured to transmit a magnification control signal, said wireless device comprising:
- a camera configured to:
  - image the item in a first magnification;
  - output first image data of the item based on the first magnification;
  - change the magnification;
  - image the item in a second magnification; and
  - output second image data of the item based on the second magnification;
- a memory; and
- a processor configured to execute instructions stored on said memory to cause said wireless device to:
  - receive the credentials;
  - establish the communication channel with the first video conference device;
  - transmit the first image data to the second video conference device;
  - receive the magnification control signal from the second video conference device;
  - instruct the camera to change the magnification based on the magnification control signal; and
  - transmit the second image data to the second video conference device.

8. The wireless device of claim 7, wherein the second video conference device is additionally configured to transmit a lighting control signal, said wireless device further comprising:
- a light configured to provide a first illumination and to provide a second illumination,
- wherein said processor configured to execute instructions stored on said memory to additionally cause said wireless device to:
  - instruct the light to provide the first illumination;
  - receive the lighting control signal;
  - instruct the light to provide the second illumination based on the lighting control signal.

9. A method of using a wireless device with a first video conference device, a second video conference device, a wide area network ("WAN") and an item, the first video conference device and the second video conference device being configured to establish a video conference over a secure communication channel over the WAN, the first video conference device being configured to provide first video data and first audio data to the second video conference device during the video conference, the second video conference device being configured to provide second video data and second audio data to the first video conference device during the video conference, the first video conference device being additionally configured to display the second video data and to output the second audio data, the second video conference device being additionally configured to display the first video data and to output the first audio data, the first video conference device additionally being configured to transmit credentials to establish a communication channel with said wireless device in response to receiving a video conference request, the second video conference device being additionally configured to transmit a magnification control signal, said method comprising:
- imaging, via a camera, the item in a first magnification;
- outputting, via the camera, first image data of the item based on the first magnification;
- transmitting, via a processor configured to execute instructions stored on a memory, a video conference request to the first video conference device;
- receiving, via the processor, the credentials;
- establishing, via the processor, the communication channel with the first video conference device;
- transmitting, via the processor, the first image data to the second video conference device;
- receiving, via the processor, the magnification control signal from the second video conference device;
- instructing, via the processor, the camera to change the magnification based on the magnification control signal;
- changing, via the camera, the magnification;
- imaging, via the camera, the item in a second magnification;
- outputting, via the camera, second image data of the item based on the second magnification; and
- transmitting, via the processor, the second image data to the second video conference device.

10. The method of claim 9, wherein the second video conference device is additionally configured to transmit a lighting control signal, said method further comprising:
- providing, via a light, a first illumination;
- receiving, via the processor, the lighting control signal; and
- instructing, via the processor, the light to provide a second illumination based on the lighting control signal.

11. A non-transitory, computer-readable media having computer-readable instructions stored thereon, the computer-readable instructions being capable of being read by a wireless device for use with a first video conference device, a second video conference device, a wide area network ("WAN") and an item, the first video conference device and the second video conference device being configured to establish a video conference over a secure communication channel over the WAN, the first video conference device being configured to provide first video data and first audio data to the second video conference device during the video conference, the second video conference device being configured to provide second video data and second audio data to the first video conference device during the video conference, the first video conference device being additionally configured to display the second video data and to output the second audio data, the second video conference device being additionally configured to display the first video data and to output the first audio data, the first video conference device additionally being configured to transmit credentials to establish a communication channel with said wireless device in response to receiving a video conference request, the second video conference device being additionally configured to transmit a magnification control signal, wherein the computer-readable instructions are capable of instructing the wireless device to perform the method comprising:
- imaging, via a camera, the item in a first magnification;
- outputting, via the camera, first image data of the item based on the first magnification;
- transmitting, via a processor configured to execute instructions stored on a memory, a video conference request to the first video conference device;
- receiving, via the processor, the credentials;
- establishing, via the processor, the communication channel with the first video conference device;
- transmitting, via the processor, the first image data to the second video conference device;

receiving, via the processor, the magnification control signal from the second video conference device;

instructing, via the processor, the camera to change the magnification based on the magnification control signal;

changing, via the camera, the magnification;

imaging, via the camera, the item in a second magnification;

outputting, via the camera, second image data of the item based on the second magnification; and transmitting, via the processor, the second image data to the second video conference device.

12. The non-transitory, computer-readable media claim 11, wherein the second video conference device is additionally configured to transmit a lighting control signal, and wherein the computer-readable instructions are capable of instructing the wireless device to perform the method further comprising:

providing, via a light, a first illumination;

receiving, via the processor, the lighting control signal; and instructing, via the processor, the light to provide a second illumination based on the lighting control signal.

* * * * *